(12) United States Patent
Derks et al.

(10) Patent No.: US 9,339,449 B2
(45) Date of Patent: *May 17, 2016

(54) SHAMPOO PREPARATIONS

(71) Applicant: DSM IP Assets B.V., Heerlen (NL)

(72) Inventors: Franciscus Johannes Marie Derks, Heythuysen (NL); Stephen Foster, Hattiesburg, MS (US); Robert Lochhead, Hattiesburg, MS (US); Adarsh Maini, Stephens City, VA (US); Dirk Weber, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/903,327

(22) Filed: May 28, 2013

(65) Prior Publication Data

US 2013/0251659 A1    Sep. 26, 2013

Related U.S. Application Data

(62) Division of application No. 12/999,740, filed as application No. PCT/EP2009/057647 on Jun. 19, 2009, now abandoned.

(60) Provisional application No. 61/129,334, filed on Jun. 19, 2008.

(51) Int. Cl.

| | | |
|---|---|---|
| *A61Q 5/02* | (2006.01) | |
| *A61K 8/85* | (2006.01) | |
| *A61K 8/88* | (2006.01) | |
| *A61K 8/72* | (2006.01) | |
| *C08G 83/00* | (2006.01) | |
| *C08G 69/44* | (2006.01) | |
| *C08L 101/00* | (2006.01) | |
| *A61Q 5/00* | (2006.01) | |
| *A61Q 5/06* | (2006.01) | |
| *A61Q 5/12* | (2006.01) | |

(52) U.S. Cl.
CPC ... *A61K 8/72* (2013.01); *A61K 8/85* (2013.01); *A61Q 5/00* (2013.01); *A61Q 5/02* (2013.01); *C08G 69/44* (2013.01); *C08G 83/005* (2013.01); *C08L 101/005* (2013.01); *A61Q 5/06* (2013.01); *A61Q 5/12* (2013.01)

(58) Field of Classification Search
CPC ............ A61K 8/72; A61K 8/85; A61Q 5/00; A61Q 5/02; A61Q 5/06; A61Q 5/12; C08G 69/44; C08G 83/005; C08L 101/005
USPC .......................................... 424/70.17, 70.11
See application file for complete search history.

(56) References Cited

U.S. PATENT DOCUMENTS

| | | | |
|---|---|---|---|
| 3,479,310 A | 11/1969 | Otto et al. | |
| 3,905,929 A | 9/1975 | Noll | |
| 3,961,042 A | 6/1976 | Green et al. | |
| 4,013,787 A | 3/1977 | Varlerberghe et al. | |
| 4,238,378 A | 12/1980 | Markusch et al. | |
| 4,515,658 A | 5/1985 | Fong | |
| 5,030,443 A * | 7/1991 | Varco et al. ........... | 424/47 |
| 5,726,137 A * | 3/1998 | Patel et al. ........... | 510/122 |
| 6,440,405 B1 | 8/2002 | Cooper et al. | |
| 6,635,262 B2 | 10/2003 | Jourdan et al. | |
| 6,638,321 B1 | 10/2003 | Genet et al. | |
| 6,730,771 B2 | 5/2004 | Van Benthem et al. | |
| 6,784,267 B1 | 8/2004 | Ward et al. | |
| 6,875,245 B2 | 4/2005 | Pavlin | |
| 6,881,400 B2 | 4/2005 | Collin | |
| 7,459,167 B1 | 12/2008 | Sengupta et al. | |
| 8,394,500 B2 * | 3/2013 | Beumer .......... | A61K 8/88 428/423.1 |
| 8,597,625 B2 * | 12/2013 | Derks ............. | A61K 8/85 424/70.17 |
| 2002/0019509 A1 | 2/2002 | Van Benthem et al. | |
| 2002/0034486 A1 | 3/2002 | Midha et al. | |
| 2002/0061832 A1 | 5/2002 | Reinehr et al. | |
| 2002/0187170 A1 | 12/2002 | Pavlin | |
| 2002/0189030 A1 | 12/2002 | Collin | |
| 2003/0057158 A1* | 3/2003 | Klomp ............ | C10L 3/00 210/698 |
| 2003/0236387 A1 | 12/2003 | Pavlin | |
| 2004/0054037 A1* | 3/2004 | Abbeele van den ... | D21H 19/62 524/47 |
| 2004/0228886 A1 | 11/2004 | Ding et al. | |
| 2005/0244353 A1 | 11/2005 | Lendlein et al. | |
| 2007/0202071 A1* | 8/2007 | Morvan ........... | A61K 8/06 424/70.17 |
| 2009/0068136 A1 | 3/2009 | Beumer et al. | |
| 2011/0165107 A1 | 7/2011 | Derks et al. | |
| 2011/0182843 A1 | 7/2011 | Derks et al. | |

FOREIGN PATENT DOCUMENTS

| | | |
|---|---|---|
| EP | 0 121 091 | 10/1984 |
| WO | WO 00/58388 | 10/2000 |

(Continued)

OTHER PUBLICATIONS van Benthem et al. (Synthesis and Characterization of Bis(2-hydroxypropyl)amine-Based Hyperbranched Polyesteramides, Macromolecules (2001) 34: 3559-3566), 8 pages.*

(Continued)

*Primary Examiner* — Brian-Yong Kwon
*Assistant Examiner* — Miriam A Levin
(74) *Attorney, Agent, or Firm* — Nixon & Vanderhye P.C.

(57) ABSTRACT

The invention relates to aqueous compositions comprising an anionic surfactant and a hyperbranched polyesteramide having at least one quaternized amine endgroup. The compositions, in particular in the form of shampoo preparations are suited for increasing the volume of hair treated therewith. Furthermore, such compositions provide styling attributes and increase the wet-combability of hair.

12 Claims, No Drawings

(56) References Cited

FOREIGN PATENT DOCUMENTS

| WO | WO 2006/013200 | | 2/2006 |
|---|---|---|---|
| WO | WO 2006/018641 | A1 | 2/2006 |
| WO | 2007/098888 | | 9/2007 |
| WO | 2007/144189 | | 12/2007 |
| WO | WO 2008/071575 | A1 | 6/2008 |

OTHER PUBLICATIONS

Froehling and Brackman (Properties and applications of poly (propylene imine) dendrimers and poly(esteramide) hyperbranched polymers, Macromol. Symp. 151, 581-589 (2000)), 9 pages.*

Moore (Surfactants and Shampoos, The Trichological Society (2001), [Retrieved from internet <URL: http://www.hairscientists.org/hairdressing-science/chemistry/surfactants >], 4 pages).*

Draelos (Essentials of Hair Care often Neglected: Hair Cleansing, International Journal of Trichology (Jan.-Jun. 2010), 2(1): 24-29; [Retrieved from internet <URL: http://www.ncbi.nlm.nih.gov/pmc/articles/PMC3002407/?report=printable>], 12 pages).*

Polymer Factory, Polyester Amide—Hybrane®, [Retrieved from internet <URL: http://www.polymerfactory.com/hyperbranched-polymers/polyester-amide-hybrane >], [Downloaded Nov. 16, 2013], 7 pages.*

U.S. Appl. No. 14/455,123, Nonfinal office action issued Dec. 2, 2015 (33 pages).*

International Search Report for PCT/EP2007/001575, mailed Jul. 16, 2007.

Written Opinion of the International Searching Authority for PCT/EP2007/001575, mailed Jul. 16, 2007.

International Search Report for PCT/EP2009/057646, mailed Sep. 30, 2009.

Office Action dated Sep. 25, 2012, issued in connection with U.S. Appl. No. 12/281,032.

International Search Report for PCT/EP2009/057647, mailed Sep. 23, 2009.

Van Benthem et al, "Synthesis and Characterization of Bis(2-hydroxypropyl)amine-Based Hyperbranched Polyesteramides", Macromolecules (2001) 34:3559-3566), 8 pages.

Froehling et al, "Properties and applications of poly (propylene imine) dendrimers and poly(esteramide) hyperbranched polymers", Macromol. Symp. 151, 581-589 (2000), 9 pages.

* cited by examiner

SHAMPOO PREPARATIONS

This application is a divisional of U.S. application Ser. No. 12/999,740 (abandoned), filed Mar. 21, 2011 (published as US-2011-0165107 A1), which is a U.S. national phase of International Application No. PCT/EP2009/057647, filed 19 Jun. 2009, which designated the U.S. and claims priority to U.S. Application No. 61/129,334, filed 19 Jun. 2008, the entire contents of each of which are incorporated herein by reference.

The invention relates to aqueous compositions comprising an anionic surfactant and a hyperbranched polyesteramide having at least one quaternized amine end-group. The compositions, in particular in the form of shampoo preparations are suited for increasing the volume of hair treated therewith. Furthermore, such compositions provide styling attributes and increase the wet-combability of hair.

People with fine or thin hair often use "volumizing" shampoos in order to add volume and body to their hair. Conventional volumizing shampoos, however, possess certain drawbacks such as, for example, a failure to provide real volume benefits as the effective ingredients are too heavy on the hair, thereby weighing it down. Another drawback associated with volumizing shampoos is their inability to provide appreciable styling attributes and wet-conditioning onto hair treated therewith.

Thus, there is an ongoing need for hair care compositions which confer volume to the hair, and in addition improve the styling attributes and enhance the wet combability of the hair and which do not leave the hair stiff or excessively sticky.

Surprisingly it has been found, that aqueous compositions comprising a hyperbranched polyesteramide having at least one quaternized amine end-group in combination with an anionic surfactant overcome the above addressed problems.

Thus, in one embodiment the invention relates to an aqueous composition comprising an anionic surfactant and an effective amount of a hyperbranched polyesteramide having at least one quaternized amine end-group.

In a particular embodiment, the aqueous composition is a shampoo preparation in particular a volumizing shampoo preparation.

The term "effective amount" means generally at least a concentration of at least 0.01% by weight based on the weight of the total composition. Preferably, a concentration of 0.01-20 wt. %, most preferred of 0.05-10 wt. %, in particular in the range of 0.5 to 2 wt.-% is used.

In another embodiment, the invention is concerned with a method of treating hair by applying a composition according to the invention. In particular, the invention relates to a method for increasing the volume of hair by applying a composition according to the invention to hair.

The invention also relates to the use of a composition according to the invention for increasing the volume of hair.

Examples of suitable anionic surfactants are the alkyl sulfates, alkyl ether sulfates, alkylaryl sulphonates, alkanoyl isethionates, alkyl succinates, alkyl sulphosuccinates, alkyl ether sulphosuccinates, N-alkyl sarcosinates, alkyl phosphates, alkyl ether phosphates, and alkyl ether carboxylic acids and salts thereof, especially their sodium, magnesium, ammonium and mono-, di- and triethanolamine salts. The alkyl and acyl groups generally contain from 8 to 18, preferably from 10 to 16 carbon atoms and may be unsaturated. The alkyl ether sulfates, alkyl ether sulphosuccinates, alkyl ether phosphates and alkyl ether carboxylic acids and salts thereof may contain from 1 to 20 ethylene oxide or propylene oxide units per molecule.

In particular, the anionic surfactants are selected from sodium oleyl succinate, ammonium lauryl sulphosuccinate, sodium lauryl sulfate, sodium lauryl ether sulfate (sodium laureth sulfate), sodium lauryl ether sulphosuccinate, ammonium lauryl sulfate, ammonium lauryl ether sulfate (ammonium laureth sulfate), sodium dodecylbenzene sulphonate, triethanolamine dodecylbenzene sulphonate, sodium cocoyl isethionate, sodium lauryl isethionate, lauryl ether carboxylic acid and sodium N-lauryl sarcosinate or mixtures thereof. Preferred anionic surfactants are sodium lauryl sulfate, sodium lauryl ether sulfate (n) EO, (where n is from 1 to 4, in particular n is 3), sodium lauryl ether sulphosuccinate (n) EO, (where n is from 1 to 4, in particular n is 3), ammonium lauryl sulfate, ammonium lauryl ether sulfate (n) EO, (where n is from 1 to 4, in particular n is 3) or mixtures thereof.

In all embodiments of the present invention the anionic surfactant is preferably selected from sodium lauryl sulfate, ammonium lauryl sulfate, sodium lauryl ether sulfate, ammonium lauryl ether sulfate, sodium lauroyl sarconisate, sodium oleylsuccinate, ammonium lauryl sulfosuccinate, sodium dodecylbenzol sulfonate and/or triethanolamine dodecylbenzol sulfonate or mixtures thereof, in particular the anionic surfactant is selected from sodium lauryl sulfate, ammonium lauryl sulfate, sodium lauryl ether sulfate and/or ammonium lauryl ether sulfate.

The total amount of the anionic surfactant in the compositions according to the invention ranges from 0.5 to 45 wt.-%, preferably from 1.5 to 35 wt.-%, more preferably from 7 to 25 wt.-%, in particular from 7 to 15 wt.-% based on the total weight of the composition.

Hyperbranched polyesteramides having quaternized amine end groups suitable for the purpose of the present invention are disclosed in WO2007098888, in particular on page 3, line 9 to page 11, line 10 which is included herein by reference.

Particular interesting hyperbranched polyesteramide having at least one quaternized amine end-group for the purpose of the present invention are obtainable by condensation of a dialkylamine of the general formula $HN(R^1R^2)$ or alcohol functional amines of the general formula $HO-R^3-N(R^1R^2)$, wherein $R^1$ and $R^2$ are di-($C_{1-20}$-alkyl)amino-$C_{1-20}$-alkyl groups or $R^1$ and $R^2$ together form a N-heterocyclic ring (preferably a 5 or 6 membered ring) and $R^3$ is $C_{1-20}$-alkyl which might also contain oxygen groups, a dicarboxylic acid or a cyclic anhydride thereof and diisopropanolamine followed by quaternization of the amino groups according to the processes as disclosed in WO2007098888 respectively in the examples of the present invention. Mixtures of dialkylamines and/or alcohol functional amines as well as mixtures of dicarboxylic acids and/or cyclic anhydrides thereof may also be used. Preferably, cyclic anhydrides are used in the condensation reaction, most preferably, the cyclic anhydrides are selected from succinic anhydride and derivatives thereof and/or phthalic anhydride and derivatives thereof such as in particular from succinic anhydride, phthalic anhydride, hexahydrophthalic anhydride and/or dodecenyl succinic anhydride and the dialkylamine is selected from bis(di(m)ethylamino)ethylamine, bis(di(m)ethylaminopropyl)amine, bis(di(m)ethylaminohexyl)amine and/or N-methylpiperazine, in particular from bis(di(m)ethylaminopropyl)amine and/or N-methylpiperazine.

Preferred alcohol functional amines of the general formula $HO-R^3-N(R^1R^2)$ are N,N-dimethylethanolamine, N,N,N'-trimethyl-N'-hydroxyethyl-bisaminoethylether, N,N-bis(3-dimethylaminopropyl)-N-isopropanolamine, N-(3-dimethylaminopropyl)-N,N-diisopropanolamine, 2-(2-dimethylaminoethoxy)ethanol and/or N,N,N'- trimethylaminoethyl-ethanolamine, in particular N,N-bis(3-dimethylaminopropyl)-N-isopropanolamine.

In all embodiments of the invention particular suitable quaternized amine end groups for the purpose of the present invention are quaternized di(m)ethylaminoethyl, di(m)ethylaminopropyl, di(m)ethylaminohexyl and/or N-methylpiperazinyl groups, in particular quaternized di(m)ethylaminopropyl and/or N-methylpiperazinyl groups.

The quaternized amine end groups of the hyperbranched polyesteramide may be prepared by reaction of the nitrogen atoms of the non-quaternized hyperbranched polyesteramide with customary quaternizing agents according to standard procedures as e.g. described in Jerry March, 'Advanced organic chemistry, $4^{th}$ edition, Wiley-Interscience p. 411ff.

Preferably, the amine end groups of the hyperbranched polyesteramides are quaternized using linear or branched ($C_1$-$C_8$) alkyl groups, in particular linear saturated ($C_1$-$C_8$) alkyl groups such as in particular with methyl and/or ethyl groups or they are quaternized using benzyl groups. The counter ion normally results from the quaternization agent but can be exchanged if necessary. Preferably, the counter ion is chloride and/or $MeSO_4^-$ and/or $EtSO_4^-$ in particular the counter ion is $MeSO_4^-$ and/or $EtSO_4^-$. Other quaternization agents are epoxides like cyclohexene oxide and glycidyl ethers and esters like glycidol and glycidylmethacrylate. Suitable agents to obtain a betaine group are chloro acetic acid and (meth)acrylic acid. In all embodiments of the invention, the preferred amine end groups are quaternized di(m)ethylaminopropyl groups or N-methylpiperazinyl groups which are quaternized with methyl or ethyl groups, most in particular the quaternized amine end groups are tri(m)ethylammoniumpropyl groups.

In another preferred embodiment, the preferred amine end groups di(m)ethylaminopropyl or N-methylpiperazinyl are quaternized with 3-chloro-2-hydroxypropyltrimethylammonium chloride.

The preferred degree of quaternization of the amine end groups of the hyperbranched polyesteramide is between 20 and 100%, more preferred between 50 and 100%, most preferred between 80 and 100% such as in particular about 95% to 100%.

The molecular weight of the hyperbranched polyesteramides according to the invention can be adjusted via the ratio of the different building blocks used, in particular by the ratio of the branching unit (i.e. diisopropanolamine) to the dicarboxylic acid or a cyclic anhydride thereof which can be easily selected by a person skilled in the art. The effect of the end blocking groups (i.e. dialkylamine/alcohol functional amine) on the molecular weight can also be calculated. However, the higher the molecular weight the less is the influence of the end blocking groups on the molecular weight of the hyperbranched polyesteramides.

Preferably, the ratio of the branching unit to the dicarboxylic acid or a cyclic anhydride thereof is selected in the range of 1.01:1.0 to 2.0:1.0, more preferably in the range of 1.05:1.0 to 1.5:1.0, most preferably in the range of 1.1:1.0 to 1.4:1.0.

Preferably, 20 to 100% of the amount of OH end groups of the core of the molecule as determined by the branching unit to dicarboxylic acid or cyclic anhydride thereof ratio is modified with end blocking groups, preferably between 50 and 98% and most preferably between 80 and 95%.

Preferably, the weight average molecular mass of the quaternized hyperbranched polyesteramides incorporated into the compositions according to the invention is between 600 g/mol and 50,000 g/mol, more preferably between 800 g/mol and 25,000 g/mol, in particular between 2000 g/mol and 25,000 g/mol, most in particular between 5000 and 20,000 g/mol.

Preferably, the number average molecular mass is between 500 g/mol and 15,000 g/mol, more preferably between 700 g/mol and 4,000 g/mol and most preferred between 1000 and 3000 g/mol.

Preferably, the average number of quaternized amine end-groups per molecule is between 2 and 250, more preferably between 3 and 50, most preferably between 6 and 25.

The molecular weights can be determined according to standard procedures via GPC.

In a particular embodiment, the hyperbranched polyesteramide comprising at least one quaternized amine end-group is obtainable by condensation of a cyclic anhydride selected from succinic anhydride, phthalic anhydride, hexahydrophthalic anhydride and/or dodecenyl succinic anhydride, in particular succinic anhydride, hexahydrophthalic anhydride and/or dodecenyl succinic anhydride, most in particular succinic anhydride and/or dodecenyl succinic anhydride, a dialkylamine selected from bis(di(m)ethylaminopropyl)amine and/or N-methylpiperazine and/or N,N-bis(3-dimethylaminopropyl)-N-isopropanolamine and diisopropanolamine followed by partial or complete quaternization the amino end groups in particular with methyl groups or by quaternization with sodium chloroacetate. Most preferably, the building blocks are selected in a ratio in order to obtain a weight average molecular mass between 5,000 g/mol and 20,000 g/mol.

In a most particular embodiment, the hyperbranched polyesteramide according to the invention is obtainable by condensation of succinic anhydride and/or dodecenyl succinic anhydride, bis(dimethylaminopropyl)amine and diisopropanolamine followed complete (i.e. 95%) quaternization of the amino end groups with methyl groups (e.g. with dimethylsulfate), with the proviso that the building blocks are selected in a ratio in order to obtain a weight average molecular mass between 5,000 g/mol and 20,000 g/mol.

The condensation reaction can be carried out in a one-step procedure at room temperature or at an elevated temperature, preferably between about 20° C. and about 120° C., to form an amide bond between the amino group of the amine and the carboxy group of the dicarboxylic acid or the anhydride thereof after which, at an elevated temperature, preferably between 120° C. and 250° C., a polyesteramide is obtained through polycondensation with water being removed, preferably through distillation. The one-step procedure can take place with or without a solvent. Suitable solvents are organic solvents, such as methyl-isobutylketone, butylacetate, toluene or xylene. The removal of water through distillation can take place at either reduced or elevated pressure, such as at a pressure higher than $1.10^5$ Pa, in a vacuum ($<1.10^5$ Pa) or azeotropically.

The compositions according to the invention preferably comprise from 50 to 98 wt.-%, preferably from 60 to 90 wt.-% of water based on the total weight of the composition.

In all embodiments of the invention the ratio of the anionic surfactant to the hyperbranched polyesteramide having at least one quaternized amine end-group is preferably in the range of 20 to 1 to 1 to 1, in particular 10 to 1 to 5 to 1, such as in particular 8 to 1.

In a preferred embodiment the compositions according to the present invention are shampoo preparations to be applied to the hair and then rinsed away.

In a particular preferred embodiment the invention relates to a shampoo preparation wherein the anionic surfactant is selected from sodium lauryl sulfate, ammonium lauryl sulfate, sodium lauryl ether sulfate and/or ammonium lauryl ether sulfate and the ratio of the anionic surfactant to the hyperbranched polyesteramide having at least one quaternized amine end-group is in the range of 20 to 1 to 1 to 1, in particular 10 to 1 to 5 to 1, such as in particular 8 to 1.

In another preferred embodiment the invention relates to a shampoo preparation wherein the anionic surfactant is selected from sodium lauryl sulfate, ammonium lauryl sulfate, sodium lauryl ether sulfate and/or ammonium lauryl ether sulfate, the average number of quaternized di(m)ethylaminopropyl and/or N-methylpiperazinyl end groups, in particular di(m)ethylaminopropyl end-groups per molecule of the hyberbranched polyesteramide is between 3 and 50 and the degree of quaternization is in the range of 80 and 100%. The amine end-groups are preferably quaternized with dimethylsulfate or diethylsulfate.

The compositions according to the invention can contain further ingredients to enhance the performance and/or consumer acceptability such as preservatives, antioxidants, fatty substances/oils, silicones, thickeners, softeners, emulsifiers, light-screening agents, antifoaming agents, moisturizers, fragrances, co-surfactants, fillers, sequestering agents, cationic-, nonionic- or amphoteric polymers or mixtures thereof, acidifying or basifying agents, dyes, colorants, pigments or nanopigments, pearlizers or opacifiers, organic or inorganic particles, viscosity modifiers, and natural hair nutrients such as botanicals, fruit extracts, sugar derivatives and/or amino acids or any other ingredients usually formulated into rinse off compositions. The necessary amounts of the adjuvants and additives can, based on the desired product, easily be chosen by a skilled artisan in this field and will be illustrated in the examples, without being limited hereto.

The shampoo preparation preferably includes co-surfactants, to help impart aesthetic, physical or cleansing properties to the compositions.

Examples of co-surfactants are nonionic surfactants, which can be included in an amount ranging from 0.5 to 8 wt.-%, preferably from 2 to 5 wt.-% based on the total weight of the preparation. For example, representative nonionic surfactants that can be included into shampoo preparations according to the invention include condensation products of aliphatic ($C_8$-$C_{18}$) primary or secondary linear or branched chain alcohols with alkylene oxides, usually ethylene oxide and generally having from 6 to 30 ethylene oxide groups. Other representative nonionic surfactants include mono- or di-alkyl alkanolamides such as e.g. coco mono- or di-ethanolamide and coco mono-isopropanolamide. Further nonionic surfactants which can be included in shampoo preparations of the invention are the alkyl polyglycosides (APGs). Typically, the APG is one which comprises an alkyl group connected (optionally via a bridging group) to a block of one or more glycosyl groups such as e.g. Oramix NS 1O ex Seppic; Plantacare 818UP, Plantacare 1200 and Plantacare 2000 ex Cognis.

Another example of a co-surfactant is an amphoteric or zwitterionic surfactant, which can be included in an amount ranging from 0.5 to about 8 wt.-%, preferably from 1 to 4 wt.-% based on the total weight of the shampoo preparation. Examples of amphoteric or zwitterionic surfactants include alkyl amine oxides, alkyl betaines, alkyl amidopropyl betaines, alkyl sulphobetaines (sultaines), alkyl glycinates, alkyl carboxyglycinates, alkyl amphoacetates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoo preparations according to the invention include lauryl amine oxide, cocodimethyl sulphopropyl betaine, lauryl betaine, cocamidopropyl betaine (CAPB), sodium cocoamphoacetate and disodium cocoamphodiacetate. A particularly preferred amphoteric or zwitterionic surfactant to be used in the shampoo preparations of the present invention is cocamidopropyl betaine.

Mixtures of any of the foregoing amphoteric or zwitterionic surfactants may also be suitable. Preferred mixtures are those of cocamidopropyl betaine with further amphoteric or zwitterionic surfactants as described above such as in particular with sodium cocoamphoacetate.

It has surprisingly been found, that shampoo preparations comprising an additional amount of an amphoteric or zwitterionic surfactant are in particular suitable for increasing the volume of hair. Thus, in a particular preferred aspect the invention relates to a shampoo preparation comprising an anionic surfactant, an amphoteric or zwitterionic surfactant and a hyperbranched polyesteramide having at least one quaternized amine end-group. Preferably, the anionic surfactant is selected from ammonium lauryl sulfate, sodium lauryl sulfate, ammonium laureth sulfate and/or sodium laureth sulfate, the amphoteric or zwitterionic surfactant is cocamidopropyl betaine and the quaternized amine end-groups are selected from quaternized di(m)ethylaminoethyl, di(m)ethylaminopropyl, di(m)ethylaminohexyl and/or N-methylpiperazinyl end groups. In particular the quaternized amine end groups are tri(m)ethylammoniumpropyl groups.

In another particular preferred aspect the anionic surfactant is selected from ammonium lauryl sulfate, sodium lauryl sulfate, ammonium laureth sulfate and/or sodium laureth sulfate, the amphoteric or zwitterionic surfactant is cocamidopropyl betaine and the average number of quaternized amine end-group selected from di(m)ethylaminopropyl and/or N-methylpiperazinyl groups, groups per molecule of the hyberbranched polyesteramide is between 3 and 50 and the degree of quaternization is in the range of 80 and 100%. The amine end-groups are preferably quaternized with dimethylsulfate and/or diethylsulfate. Most preferably, the quaternized amine end groups are tri(m)ethylammoniumpropyl groups.

The total amount of surfactant (including any co-surfactant, and/or any emulsifier) in a shampoo preparation according to invention is generally from 1 to 50%, preferably from 2 to 40%, more preferably from 5 to 25%, in particular from 9 to 15 wt.-% based on the total weight of the composition.

In a further preferred embodiment, the compositions according to the invention also comprise a hydrotrope. A hydrotrope is a substance that improves the solubility of surfactants in water. Examples of hydrotropes are sodium xylene sulfonate, ammonium xylene sulphonate, sodium p-toluene sulfonate, sodium chlorobenzene sulfonate, sodium salicylate, proline, pyrogallol, resorcinol and urea. In all embodiments of the invention preferably sodium xylene sulfonate is used as hydrotrope. The total amount of the hydrotrope in the compositions according to the invention ranges from 0.5 to 30 wt.-%, preferably from 1 to 20 wt.-%, in particular from 1 to 5 wt.-% based on the total weight of the composition.

Particular preferred shampoo preparations according to the invention comprise an anionic surfactant, a hyperbranched polyesteramide having at least one quaternized amine end-group, an amphoteric or zwitterionic surfactant and a hydrotrope. Preferably, the anionic surfactant is selected from ammonium lauryl sulfate, sodium lauryl sulfate, ammonium laureth sulfate and/or sodium laureth sulfate, the amphoteric or zwitterionic surfactant is cocamidopropyl betaine and the hydrotrope is sodium xylene sulfonate. In a particular preferred embodiment, the quaternized amine end groups are tri(m)ethylammoniumpropyl groups.

The shampoo preparations according to the invention may also contain cationic polymers for further enhancing conditioning performance. Suitable cationic polymers may be homopolymers which are cationically substituted or may be formed from two or more types of monomers. The weight average molecular weight (Mw) of the polymers will generally be between 100 000 and 2 million Daltons. Suitable cationic polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have $C_1$-$C_7$ alkyl groups, more preferably $C_{1-3}$ alkyl groups. Other suitable spacers include vinyl esters, vinyl alcohol, maleic anhydride, propylene glycol and ethylene glycol.

Cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

The cationic polymers can comprise mixtures of monomer units derived from amine- and/or quaternary ammonium-substituted monomer and/or compatible spacer monomers.

Suitable cationic polymers include, for example:
cationic diallyl quaternary ammonium-containing polymers including, for example, dimethyldiallylammonium chloride homopolymer and copolymers of acrylamide and dimethyldiallylammonium chloride, referred to in the industry (CTFA) as Polyquaternium 6 and Polyquaternium 7, respectively;
mineral acid salts of amino-alkyl esters of homo- and co-polymers of unsaturated carboxylic acids having from 3 to 5 carbon atoms, (as described in U.S. Pat. No. 4,009,256)
cationic polyacrylamides (as described in WO95/22311).

Other cationic polymers that can be used include cationic polysaccharide polymers, such as cationic cellulose derivatives, cationic starch derivatives, and cationic guar gum derivatives.

Another type of cationic cellulose includes the polymeric quaternary ammonium salts of hydroxyethyl cellulose reacted with trimethyl or lauryl dimethyl ammonium-substituted epoxide, referred to in the industry (CTFA) as Polyquaternium 10 and Polyquaternium 24 respectively. These materials are available from the Amerchol Corporation, for instance under the trade name Ucare Polymer JR or Ucare Polymer LM.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581). A particularly suitable type of cationic polysaccharide polymer that can be used is a cationic guar gum derivative, such as guar hydroxypropyltrimethylammonium chloride or Hydroxypropyl guar hydroxypropyltrimethylammonium chloride (commercially available from Rhodia in their JAGUAR trademark series). Examples of such materials are JAGUAR C135, JAGUAR C145, JAGUAR C17; JAGUAR C162 and JAGUAR Excel.

Mixtures of any of the above cationic polymers may be used.

The cationic polymer(s) will generally be present in a shampoo preparation of the present invention at levels of from 0.01 to 5 wt.-%, preferably from 0.05 to 1 wt.-%, more preferably from 0.08 to 0.5 wt.-% by total weight of cationic polymer based on the total weight of the composition.

Preferably a shampoo preparation of the invention further comprises a suspending agent. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives, since these impart pearlescence to the composition. Polyacrylic acid is available commercially as Carbopol 420, Carbopol 488 or Carbopol 493. Polymers of acrylic acid cross-linked with a polyfunctional agent may also be used; they are available commercially as Carbopol 910, Carbopol 934, Carbopol 941, Carbopol 980 and Carbopol Ultrez 10 Polymer. Examples of suitable copolymers of a carboxylic acid containing monomer and acrylic acid esters are Carbopol 1342, Carbopol Ultrez 20 or Carbopol Ultrez 21, Pemulen TR1 or Pemulen TR2. All Carbopol or Pemulen (trademark) materials are available from Noveon Consumer Specialities.

A suitable heteropolysaccharide gum is xanthan gum, for example Keltrol-types or Kelzan-types from Kelco, Vanzan NF from RT Vanderbilt Inc. or Rhodicare-types from Rhodia.

Mixtures of any of the above suspending agents may be used. Preferred is a mixture of cross-linked polymer of acrylic acid and crystalline long chain acyl derivative.

The suspending agent(s) will generally be present in a shampoo preparation of the invention at levels of from 0.1 to 10 wt.-%, preferably from 0.5 to 6 wt.-%, more preferably from 0.9 to 4 wt.-% by total weight of suspending agent based on the total weight of the composition.

The shampoo preparations of the invention may comprise further conditioning agents to further optimize wet and dry conditioning benefits.

Particularly preferred further conditioning agents are silicone emulsions. Suitable silicone emulsions include those formed from silicones such as polydiorganosiloxanes, in particular polydimethylsiloxanes which have the CTFA designation dimethicone, polydimethyl siloxanes having hydroxyl end groups which have the CTFA designation dimethiconol, and amino-functional polydimethyl siloxanes which have the CTFA designation amodimethicone. Suitable silicone emulsions for use in compositions of the invention are available from suppliers of silicones such as Dow Corning and GE Silicones. The use of such pre-formed silicone emulsions is preferred for ease of processing and control of silicone particle size. Such pre-formed silicone emulsions will typically additionally comprise a suitable emulsifier such as an anionic or nonionic emulsifier, or mixture thereof, and may be prepared by a chemical emulsification process such as emulsion polymerisation, or by mechanical emulsification using a high shear mixer. Preformed silicone emulsions having a Sauter mean droplet diameter ($D_{3,2}$) of less than 0.15 micrometers are generally termed microemulsions. Examples of suitable pre-formed silicone emulsions include emulsions DC2-1766, DC2-1784, DC-1785, DC-1786, DC-1788 and microemulsions DC2-1865 and DC2-1870, all available from Dow Corning. These are all emulsions/microemulsions of dimethiconol. Also suitable are amodimethicone emulsions such as DC939 (from Dow Corning) and SME253 (from GE Silicones). Also suitable are silicone emulsions in which certain types of surface active block copolymers of a high molecular weight have been blended with the silicone emulsion droplets, as described for example in WO03/094874.

Silicone will generally be present in a composition of the invention at levels of from 0.05 to 10 wt.-%, preferably 0.05 to 5 wt.-%, more preferably from 0.5 to 2 wt.-% by total weight of silicone based on the total weight of the composition.

The shampoo preparations according to the invention may further contain anti dandruff agents. Examples of anti-dandruff agents which may be used are cimbazole, octopirox and zinc pyrithione. Customary film formers include, for example, chitosan, microcrystalline chitosan, quaternized chitosan, polyvinylpyrrolidone, vinylpyrrolidone/vinyl acetate copolymers, polymers of quaternary cellulose derivatives containing a high proportion of acrylic acid, collagen, hyaluronic acid and salts thereof and similar compounds.

The shampoo preparations according to the invention may further contain UV-filter substances. Examples of UV-filter substances suitable for the incorporation into the compositions according to the invention include benzophenones such as e.g. benzophenones-4 or benzophenones-3, acrylates such as 2-ethylhexyl 2-cyano-3,3-diphenylacrylate (octocrylene, PARSOL® 340), cinnamate derivatives such as ethylhexyl methoxycinnamate (PARSOL® MCX), benzalmalonate derivatives bond to siloxanes such as e.g. polysilicones-15 (PARSOL® SLX), salicylate derivatives such as isopropyl-benzyl salicylate, benzyl salicylate, butyl salicylate, ethylhexyl salicylate (PARSOL® EHS, Neo Heliopan OS), isooctyl salicylate or homomethyl salicylate (homosalate, PARSOL® HMS, Neo Heliopan HMS), benzotriazole derivatives such as sodium benzotriazolyl butylphenol sulfonate, imidazole derivatives such as e.g. 2-phenyl benzimidazole sulfonic acid and its salts (PARSOL® HS), dibenzoylmethane derivatives such as (avobenzone, Parsol® 1789) without being limited thereto.

In another embodiment the invention relates to the use of a hyperbranched polyesteramide having at least one quaternized amine end-group with all the preferences and definitions as given above for increasing the volume of hair.

The invention is further illustrated with reference to the following, non-limiting examples, in which all percentages are by weight based on total weight unless otherwise specified.

EXAMPLE 1

Synthesis of a Quaternary Amine Functional Hyper Branched Polyester Amide 305 g of bis-(N,N-dimethyl aminopropyl)amine and 350 g of molten hexahydro phthalic anhydride were added to a glass reactor equipped with stirrer and condenser, and which can be heated by oil. The mixture was slowly heated to 180° C. and ½ h after the start, 145 g molten diisopropanolamine was added and 1½ h later vacuum was applied to remove the reaction water. After 5 h the mixture was cooled and a glassy polymer with a Mn=1600 was obtained. Afterwards, 50 g of the polymer was dissolved in 72.4 g water and at room temperature 22.4 g of dimethyl sulfate was slowly added. First the mixture was turbid but within 10 min the temperature raised to about 50° C. and the mixture became clear. After 24 h the fully quaternized polymer solution was ready for use.

EXAMPLE 2

Synthesis of a Quaternary Amine Functional Hyper Branched Polyester Amide 232 g of bis-(N,N-dimethyl aminopropyl)amine and 458.1 g of molten dodecenyl succinic anhydride were added to a glass reactor equipped with stirrer and condenser, and which can be heated by oil. The mixture was slowly heated to 180° C. and ½ h after the start, 172 g molten diisopropanolamine was added and 1½ h later vacuum was applied to remove the reaction water. After 5 h the mixture was cooled and a viscous polymer was obtained. 50 g of the polymer was dissolved in 67.6 g water and at room temperature 17.6 g of dimethyl sulfate was slowly added. First the mixture was turbid but within 10 min the temperature raised to about 50° C. and the mixture became clear. After 24 h the fully quaternized polymer solution was ready for use.

EXAMPLE 3

Volume UP Performance I

A formulation containing 8 wt.-% SLES-3, 1.3 wt.-% CAPB and 2.7 wt.-% sodium xylene sulfonate (SXS) and 1 wt.-% of the hyperbranched polyesteramide having at least one quaternized amine end-group of example 2 in water was prepared.

The control consists of 8 wt.-% SLES-3, 1.3 wt.-% CAPB and 2.7 wt.-% sodium xylene sulfonate (SXS) in water.

The cut hair was pre-washed twice using 1 ml of a 14/2 SLES/CAPB solution per 2 g hair. Afterwards 0.5 g of hair was placed into 50 mL Falcon centrifuge tubes with a hole cut out in the bottom. The samples were pre-rinsed with DI Water to allow hairs to settle uniformly. A nylon mesh filter was used to cover the hole in the centrifuge tubes. After pre-rinse the samples were allowed to dry for 45 minutes. Initial volumes were recorded using the volumetric notation of the tube. Then 2.5 mL of DI water were added to the samples, followed by 0.5 mL of the formulation respectively the control, followed by another 2.5 mL of DI water. The samples were agitated by hand for thirty seconds and then drained. Volumes were then again recorded using the volumetric notation of the tube. The samples were then diluted further by adding 5 mL of DI water and agitating for thirty seconds and draining. This was performed 4 times for each sample. Volumes were recorded using the volumetric notation of the tube. Finally, the samples were placed into a dry oven and allowed to dry for 18 hours at 40° C. Afterwards the final volumes were recorded using the volumetric notation of the tube.

TABLE 1

Results of the hair volume measurement

|  | initial (ml) | after wash | after 4 rinses | final |
|---|---|---|---|---|
| Control | 12 | 10 | 9.2 | 9.3 |
| Formulation | 11.5 | 12.8 | 14.1 | 12.0 |

As to be seen in table 1, the control shows a decrease of volumes while the formulation according to the invention formulation shows an increased hair volume.

| Volume up performance II | | | |
| --- | --- | --- | --- |
| INCI Nomenclature | Formula A | Formula B | Formula C |
| 1 Sodium Laureth Sulfate | 9.8 | 9.8 | 9.8 |
| Cocamidopropyl betaine | 2 | 2 | 2 |
| Sodium Chloride | 1.5 | 1.5 | 1.5 |
| Citric Acid | 0.20 | 0.20 | 0.20 |
| Fragrance | 0.2 | 0.2 | 0.2 |
| Sodium Benzoate | 0.5 | 0.5 | 0.5 |
| Polymer of example 2 | 0.5 | | |
| Hydroxypropylguarhydroxypropyltrimonium chloride | | 0.3 | |
| Water | Ad. 100 | Ad. 100 | Ad. 100 |

The Shampoos according to formula E-G were used to carry out a Volume test detecting the visible hair volume according to the following procedure:

10 standard hair switches per product are used (4 g, length L=14 cm). Each switch is preconditioned in water for 15 minutes, cleaned twice with 14% sodium alkyl (C12-14) polyethylene glycol ether (2 EO)-sulphate, soaked for 1 minute and rinsed thoroughly with water (37° C.) for 1 minute. After conditioning for 24 hours at a temperature of 22° C.±1° C. and 55%±5% rel. humidity digital pictures of the switches rotating in steps of 6° are taken. The regarding singular shapes of the switch are calculated by digital photo analyses (Initial Value).

Afterwards, the test product is applied with a defined amount per switch, massaged-in for 1 minute, kept that way for two minutes and rinsed with water for one minute. The wet switches are conditioned for 24 hours at room temperature (22° C.±1° C. and 55%±5% rel. humidity).

Once again, the hair switch is measured and calculated by digital image analysis to obtain the measuring value.

In, five consecutive washing cycles were performed and after each hair wash the resulting volume of the switch were measured.

After the 5 cycles, the following volumes were detected:

| | Volume (in % from Initial Volume) |
| --- | --- |
| Formula A | 163 |
| Formula B | 121 |
| Formula C | 140 |

The best volume increase was found for formula A, followed by Formula C (blank). The weakest Volume up performance was found for formula B.

EXAMPLE 4

| Clear Shampoo with volumizing effect | |
| --- | --- |
| INCI Nomenclature | wt. % |
| 1 Sodium Laureth Sulfate | 10.00 |
| Ammonium Lauryl Sulfate | 5.00 |
| Water | 40.00 |
| Cocamidopropyl Betaine | 2.50 |
| Borago Officinalis Seed Oil & Tocopherol & Ascorbyl Palmitate | 0.30 |
| PEG-40 Hydrogenated Castor Oil | 0.50 |
| Fragrance | 0.30 |
| 2 Panthenol | 1.00 |
| Disodium EDTA | 0.10 |
| Water | 10.00 |
| Sodium benzoate | 0.50 |
| Citric acid | 0.2 |
| Polymer of example 2 | 2.50 |

| Clear Shampoo with volumizing effect | |
| --- | --- |
| INCI Nomenclature | wt. % |
| 3 Sodium Chloride | 2.00 |
| PEG-150 Pentaerythrityl Tetrastearate | 3.00 |
| Water | ad. 100 |

Add all ingredients of part 1) and mix intensively until a homogeneous solution is obtained. Then, add the water under slow agitation and wait until the foam has disappeared. Finally, add carefully the thickening agent like Sodium Chloride or Crothix LVR.

EXAMPLE 5

| Hydrating Shampoo with volumizing effect | |
| --- | --- |
| INCI Nomenclature | wt. % |
| 1 Sodium Myreth Sulfate | 10.00 |
| Ethylhexyl Methoxycinnamate | 0.30 |
| Sodium Benzoate | 0.50 |
| Citric Acid | 0.20 |
| Panthenol | 1.00 |
| PEG-7 Glyceryl Cocoate | 2.00 |
| Cocamidopropyl Betaine | 3.50 |
| Glycol Distearate & Glycerin and Laureth-4 & Cocamidopropyl Betaine | 2.00 |
| Disodium EDTA | 0.10 |
| Parfum | 0.80 |
| Polyquaternium-10 | 0.10 |
| Decyl Glucoside | 10.00 |
| 2 Sodium Chloride | 1.50 |
| Polymer of example 1 | 2.00 |
| PEG-18 Glyceryl Oleate/Cocoate | 1.00 |
| Aqua (water) | Ad 100 |

Add all ingredients of part 1 and mix intensively until a homogeneous solution is obtained. Add the water under slow agitation and wait until the foam has disappeared. Than add carefully the thickening agent like Sodium Chloride or Crothix LVR.

EXAMPLE 6

| Hydrating Shampoo for Color Protection with volumizing effect | |
| --- | --- |
| INCI Nomenclature | wt. % |
| 1 Sodium Laureth Sulfate | 15.00 |
| Polysilicone-15 | 0.30 |
| Methylchloroisothiazolinone & Methylisothiazolinone | 0.10 |
| Panthenol | 1.00 |
| PEG-7 Glyceryl Cocoate | 2.00 |
| Cocamidopropyl Betaine | 3.50 |
| Glycol Distearate & Glycerin and Laureth-4 & Cocamidopropyl Betaine | 2.00 |
| Disodium EDTA | 0.10 |
| Fragrance | 0.80 |
| Polyquaternium-10 | 0.10 |
| Decyl Glucoside | 10.00 |
| 2 Aqua (water) | Ad 100 |
| Polymer of example 2 | 1.50 |
| Sodium Chloride | 1.50 |
| PEG-18 Glyceryl Oleate/Cocoate | 1.00 |

Add all ingredients of part 1 and mix intensively until a homogeneous solution is obtained. Add the water under slow agitation and wait until the foam has disappeared. Than add carefully the thickening agent like Sodium Chloride or Crothix LVR.

EXAMPLE 7

| Anti Dandruff Shampoo with volumizing effect | |
|---|---|
| INCI Nomenclature | wt. % |
| Aqua (water) | Ad 100 |
| Ammonium laureth sulfate | 10.00 |
| Ammonium lauryl sulfate | 5.00 |
| Glycol disearate | 1.00 |
| Dimethicone | 1.00 |
| Cetyl alcohol | 0.50 |
| Cocamide MEA | 3.00 |
| ZPT | 1.00 |
| Guar hydroxypropyltrimonium chloride | 0.20 |
| Hydrogenated polydecene | 1.00 |
| Polyquaternium 10 | 0.30 |
| PEG 7m | 0.50 |
| Trimethylpropane tricaprylate/tricaprate | 1.00 |
| Preservative | q.s. |
| Fragrance | 0.30 |
| E 104, E 110, E 132 | 0.02 |
| Polymer of example 2 | 1.00 |

EXAMPLE 8

| Conditioner Shampoo with volumizing effect | |
|---|---|
| INCI Nomenclature | wt. % |
| Aqua (water) | Ad 100 |
| Sodium laureth sulfate | 8.00 |
| Cocamidopropyl betaine | 1.50 |
| Sodium chloride | 2.50 |
| Glycol distearate | 1.00 |
| Glycerin | 2.00 |
| Dimethiconol | 0.50 |
| Fragrance | 0.50 |
| Coco-glucoside | 3.00 |
| Carbomer | 0.10 |
| Arginine | 0.05 |
| Glyceryl oleate | 0.05 |
| Glyceryl stearate | 1.00 |
| Guar hydroxypropyltrimonium chloride | 0.10 |
| Panthenol | 1.00 |
| Disodium EDTA | 0.05 |
| Preservative | q.s. |
| Hydrolyzed keratin | 0.10 |
| Citric acid/sodium hydroxide | q.s |
| Polymer of example 1 | 0.50 |
| E 102, E 110, FD&C blue | 0.01 |

EXAMPLE 9

| Shampoo with plant extracts and with volumizing effect | |
|---|---|
| INCI Nomenclature | wt. % |
| Aqua (water) | Ad 100 |
| Sodium laureth sulfate | 10.00 |
| Lauryl glucoside | 6.00 |
| Cocamidopropyl betaine, | 2.00 |
| Propylene glycol | 2.00 |
| Perfume oil | 1.25 |

| Shampoo with plant extracts and with volumizing effect | |
|---|---|
| INCI Nomenclature | wt. % |
| Sodium citrate | 0.25 |
| Sodium benzoate | 0.20 |
| Panthenol | 1.00 |
| Sodium formate | 0.20 |
| Polyquaternium-10 | 0.20 |
| Hydroxypropyl guar hydroxypropyltrimonium chloride | 0.05 |
| PEG-35 castor oil | 1.00 |
| Maris sal | 1.25 |
| Polysorbate 20 | 1.00 |
| Tocopheryl acetate | 0.20 |
| *Prunus armeniaca* | 0.20 |
| *Echinacea purpurea* | 0.05 |
| Retinyl palmitate | 0.05 |
| Tocopherol | 0.05 |
| Linoleic acid | 0.20 |
| Preservative | 1.00 |
| Polymer of example 2 | 0.01-20 |
| CI77891 | 0.02 |

EXAMPLE 10

| Gloss Shampoo with volumizing effect | |
|---|---|
| INCI Nomenclature | wt. % |
| Aqua (water) | Ad 100 |
| Sodium laureth sulfate | 8.700 |
| Disodium cocoamphodiacetate | 6.00 |
| PEG-4 Distearylether & Sodium Laureth sulfate & Distearylether & Dicaprylylether | 6.00 |
| Acrylates Copolymer | 1.50 |
| Cocamidopropylpyl betaine | 2.00 |
| Sodium Lauroyl Glutamate | 2.00 |
| Polysilicone-15 | 1.00 |
| Dimethicone | 0.80 |
| Phytantriol | 0.25 |
| Allantoin | 0.50 |
| Mica | 0.10 |
| Preservative | q.n. |
| Polymer of example 1 | 3.00 |
| Fragrance | 0.40 |
| Adjustment of pH with NaOH/Citric acid to 6-6.5 | |

We claim:

1. A method of treating hair to increase the volume thereof comprising applying a composition to said hair, the composition comprising an anionic surfactant, an amphoteric or zwitterionic surfactant and an effective amount of a hyperbranched polyesteramide having at least one quaternized amine end-group, wherein the hyperbranched polyesteramide having at least one quaternized amine end-group is obtainable by condensation of a dialkylamine of the general formula $HN(R^1R^2)$ and/or an alcohol functional amines of the general formula $HO-R^3-N(R^1R^2)$, wherein $R^1$ and $R^2$ are di-($C_{1-20}$-alkyl)amino-$C_{1-20}$-alkyl groups or $R^1$ and $R^2$ together form a N-heterocyclic ring and $R^3$ is $C_{1-20}$-alkyl which optionally also contain oxygen groups, a dicarboxylic acid or a cyclic anhydride thereof and diisopropanolamine followed by quaternization of the amino groups.

2. The method of claim 1, wherein the aqueous composition is a volumizing shampoo preparation.

3. The method of claim 1, wherein the anionic surfactant is selected from sodium lauryl sulfate, ammonium lauryl sulfate, sodium lauryl ethersulfate, ammonium lauryl ethersulfate, sodium lauroyl sarconisate, sodium oleylsuccinate, ammonium lauryl sulfosuccinate, sodium dodecylbenzol sulfonate and/or triethanolamido decylbenzol sulfonate.

4. The method of claim 3, wherein the anionic surfactant is selected from sodium lauryl sulfate, ammonium lauryl sulfate, sodium lauryl ether sulfate and/or ammonium lauryl ether sulfate.

5. The method of claim 1, wherein the amount of the anionic surfactant is in the range of 7 to 25 wt % based on the total weight of the composition.

6. The method of claim 1, wherein the ratio of the anionic surfactant to the hyperbranched polyesteramide having at least one quaternized amine end-group is in the range of 10 to 1 to 5 to 1.

7. The method of claim 1, wherein the quaternized amine end-groups are selected from quaternized di(m)ethylaminoethyl, di(m)ethylaminopropyl, di(m)ethylaminohexyl and/or N-methylpiperazinyl groups.

8. The method of claim 1, wherein the degree of quaternization of the amine end-groups is in the range of about 80 to 100%.

9. The method of claim 1, wherein the amount of the hyperbranched polyesteramide having at least one quaternized amine end-group is in the range of 0.05-10 wt % based on the total weight of the composition.

10. The method of claim 1, wherein the amphoteric or zwitterionic co-surfactant is cocamidopropyl betaine.

11. The method of claim 1, wherein an additional amount of a hydrotrope is present.

12. The method of claim 11, wherein the hydrotrope is sodium xylene sulfonate.

* * * * *